United States Patent
Suzuki et al.

(10) Patent No.: US 11,819,230 B2
(45) Date of Patent: Nov. 21, 2023

(54) SURGICAL TOOL WITH REDUCED ACTUATION FORCE

(71) Applicant: OLYMPUS MEDICAL SYSTEMS CORP., Tokyo (JP)

(72) Inventors: Tatsuya Suzuki, Hachioji (JP); Hiroshi Minami, Chofu (JP); Hideo Sanai, Hachioji (JP); Shunsuke Matsui, Hachioji (JP); Yuki Amano, Hadano (JP)

(73) Assignee: Olympus Medical Systems Corp., Tokyo (JP)

( * ) Notice: Subject to any disclaimer, the term of this patent is extended or adjusted under 35 U.S.C. 154(b) by 110 days.

(21) Appl. No.: 17/552,681

(22) Filed: Dec. 16, 2021

(65) Prior Publication Data
US 2022/0273325 A1 Sep. 1, 2022

Related U.S. Application Data

(60) Provisional application No. 63/154,375, filed on Feb. 26, 2021.

(51) Int. Cl.
*A61B 17/29* (2006.01)
*A61B 17/02* (2006.01)

(52) U.S. Cl.
CPC .......... *A61B 17/02* (2013.01); *A61B 17/2909* (2013.01); *A61B 2017/292* (2013.01);
(Continued)

(58) Field of Classification Search
CPC ........ A61B 17/2841; A61B 2017/2913; A61B 17/2922; A61B 2017/2915; A61B 2017/2916; A61B 2017/293; A61B 2017/2934; A61B 2017/2936; A61B 17/2909; A61B 2017/291; A61B 2017/2911; A61B 2017/2912; A61B 2017/2914; A61B 2017/2917; A61B 2017/2918; A61B 2017/2919; A61B 2017/292; A61B 2017/294; A61B 2017/295

See application file for complete search history.

(56) References Cited

U.S. PATENT DOCUMENTS 5,478,351 A * 12/1995 Meade ............... A61B 17/2909
606/174
8,398,674 B2 * 3/2013 Prestel ................... A61B 17/29
606/174

(Continued)

*Primary Examiner* — Timothy J Neal
*Assistant Examiner* — Mitchell Brian Hoag
(74) *Attorney, Agent, or Firm* — Morgan, Lewis & Bockius LLP

(57) ABSTRACT

A surgical tool including a housing having a proximal end and a distal end the housing including a guide rail. The tool also includes a yoke slidably coupled to the housing, a handle pivotally coupled to the housing, and a link coupling the handle to the housing, the link having a first end and a second end, the first end of the link rotatably coupled to the handle and the second end of the link rotatably coupled to the yoke and slidable within the guide rail. The tool further includes a yoke pivot pin pivotably coupling the second end of the link to the yoke and a handle pivot pin coupling the link to the handle, wherein the handle pivot pin is disposed proximal compared to the yoke pivot pin.

21 Claims, 13 Drawing Sheets

(52) U.S. Cl.
CPC ... *A61B 2017/293* (2013.01); *A61B 2017/294* (2013.01); *A61B 2017/2911* (2013.01); *A61B 2017/2916* (2013.01); *A61B 2017/2919* (2013.01); *A61B 2017/2945* (2013.01)

(56) References Cited

U.S. PATENT DOCUMENTS

| | | | | |
|---|---|---|---|---|
| 8,540,624 | B2* | 9/2013 | Bissinger | A61B 17/2909 600/101 |
| 9,241,728 | B2 | 1/2016 | Price et al. | |
| 2006/0217742 | A1* | 9/2006 | Messerly | A61B 17/1285 606/139 |
| 2007/0123933 | A1* | 5/2007 | Johnson | A61B 17/2909 606/205 |
| 2010/0030239 | A1* | 2/2010 | Viola | A61B 17/0469 606/144 |
| 2011/0264093 | A1* | 10/2011 | Schall | A61B 18/1445 606/52 |
| 2011/0301592 | A1* | 12/2011 | Kerr | A61B 17/282 606/41 |
| 2012/0184972 | A1* | 7/2012 | Lam | A61B 17/0401 606/144 |
| 2014/0100600 | A1* | 4/2014 | Kendrick | A61B 17/320092 606/205 |
| 2014/0135805 | A1* | 5/2014 | Windgassen | A61B 17/295 606/205 |
| 2014/0257252 | A1* | 9/2014 | Ishida | A61B 17/00234 606/1 |
| 2014/0276738 | A1* | 9/2014 | Price | A61B 18/1445 606/33 |
| 2015/0073394 | A1* | 3/2015 | Schiele | A61B 18/1445 606/1 |
| 2015/0201953 | A1* | 7/2015 | Strobl | A61B 18/1445 606/206 |
| 2016/0143657 | A1* | 5/2016 | Estera | A61B 17/26 606/169 |
| 2016/0157926 | A1* | 6/2016 | Boudreaux | A61B 17/295 606/170 |
| 2017/0196635 | A1* | 7/2017 | Brennan | A61B 17/2909 |
| 2020/0305962 | A1* | 10/2020 | Ward | A61B 17/285 |
| 2022/0280225 | A1* | 9/2022 | Worrell | A61B 18/1445 |

\* cited by examiner

SURGICAL TOOL WITH REDUCED ACTUATION FORCE

RELATED APPLICATION DATA

This application is based on and claims priority under 35 U.S.C. § 119 to U.S. Provisional Application No. 63/154,375, filed Feb. 26, 2021, the entire contents of which are incorporated herein by reference.

FIELD OF THE INVENTION

The present invention generally relates to a surgical tool having a reduced actuation force, and more particularly, a surgical tool having a handle requiring a reduced actuation force for actuating a grasping instrument.

BACKGROUND OF THE INVENTION

Surgical tools that grip and/or cut tissue by squeezing a handle, such as laparoscopic surgical tools, may be actuated by movement of a yoke. For example, hand-held surgical tools are commonly used by surgeons for minimally invasive, robotic, and open surgeries. These surgical tools may include an end instrument assembly that is actuated by a handle that the surgeon squeezes. However, these tools often require significant force on the handle to actuate the yoke that in turn actuates a grasper assembly disposed at the end of the tool. Further, the mechanisms required to transmit the force from the handle to actuate the grasper assembly can be bulky and require significant space within the housing of the tool.

BRIEF SUMMARY OF THE INVENTION

Embodiments of the present invention are directed to a surgical tool having a housing having a proximal end and a distal end, the housing including a guide rail, a yoke slidably coupled to the housing, a handle pivotally coupled to the housing, a link coupling the handle to the housing, the link having a first end and a second end, the first end of the link rotatably coupled to the handle and the second end of the link rotatably coupled to the yoke and slidable within the guide rail, a yoke pivot pin pivotably coupling the second end of the link to the yoke, and a handle pivot pin coupling the link to the handle, wherein the handle pivot pin is disposed proximal compared to the yoke pivot pin.

In some embodiments, the guide rail is curved. The guide rail may have a proximal end and a distal end, the proximal end of the guide rail being disposed below the distal end of the guide rail. The guide rail may include a channel and the yoke pivot pin is disposed through the guide rail such that the yoke pivot pin slides within the channel.

In some embodiments, the yoke pivot pin is disposed distal compared to the handle pivot pin. The yoke pivot pin may include a first end and a second end each being tapered. The yoke pivot pin may extend through the yoke, the link, and the guide rail.

In some embodiments, the handle pivot pin is disposed proximate the proximal end of the housing compared to the yoke pivot pin. The handle may include a top and a bottom and the handle pivot pin is disposed closer to the bottom of the handle than the yoke pivot pin. The handle may be coupled to the housing at a pivot point and the handle includes a top and a bottom, the handle pivot pin being disposed closer to the bottom of the handle than the pivot point.

In some embodiments, the handle is coupled to the housing at a pivot point and the handle includes a top and a bottom, the yoke pivot pin being disposed closer to the bottom of the handle than the pivot point. The handle may have an initial position and an actuated position, the actuated position being when the handle is disposed proximate the proximal end of the housing compared to when the handle is in the initial position. Pivoting of the handle towards the proximal end of the housing may move the yoke distally.

In some embodiments, the surgical tool further includes a guide aperture that extends through the yoke, the guide aperture configured to receive the yoke pivot pin such that the yoke pivot pin is movable within the guide aperture during actuation of the handle.

In some embodiments, the yoke pivot pin includes a ring member configured to contact the guide rail.

In some embodiments, the guide rail includes a low-friction coating formed on a region of the guide rail where the yoke pivot pin contacts the guide rail.

In some embodiments, the surgical tool further includes a grasper assembly disposed at a distal end of a shaft, the shaft extending form the distal end of the housing, wherein movement of the handle results in movement of the yoke causing actuation of the grasper assembly.

In some embodiments, the surgical tool further includes a motor coupled to the yoke and configured to move the yoke.

In some embodiments, the surgical tool further includes an elongated shaft extending from the distal end of the housing and a grasping instrument disposed on a distal end of the elongated shaft, the grasping instrument coupled to the yoke such that movement of the yoke causes actuation of the grasping instrument.

Another embodiment of the present invention may provide a surgical tool having a housing having a proximal end and a distal end, the housing including a guide rail, a yoke slidably coupled to the housing between the proximal end and the distal end, a handle pivotally coupled to the housing, wherein pivoting of the handle causes the yoke to move proximally and distally, a link coupling the handle to the housing, the link having a first end and a second end, the first end of the link rotatably coupled to the handle and the second end of the link rotatably coupled to the housing by a yoke pivot pin, the yoke pivot pin being slidable within the guide rail and coupled to the yoke and a handle pivot pin coupling the link to the handle, wherein the handle pivot pin is disposed proximal to the yoke pivot pin. The guide rail may be curved and may include a channel and the pivot pin may be disposed through the guide rail such that the pivot pin slides within the channel.

Another embodiment of the present invention may provide a laparoscopic surgical tool having a housing having a proximal end and a distal end, the housing including a guide rail and a shaft extending from a portion of the housing proximate the proximal end to the distal end, a yoke slidably coupled to the housing between the proximal end and the distal end, a handle pivotally coupled to the housing, wherein pivoting of the handle causes the yoke to move proximally and distally, a grasper assembly disposed at a distal end of the shaft, the grasper assembly configured to actuate upon movement of the yoke, a link coupling the handle to the housing, the link having a first end and a second end, the first end of the link rotatably coupled to the handle and the second end of the link rotatably coupled to the housing and slidable within the guide rail, a handle pivot pin coupling the link to the handle, wherein the handle pivot pin is disposed proximal to the yoke pivot pin. The guide rail may be curved and may include a channel and the yoke pivot pin may be disposed through the guide rail such that the yoke pivot pin slides within the channel.

BRIEF DESCRIPTION OF THE SEVERAL VIEWS OF THE DRAWINGS

The foregoing summary, as well as the following detailed description of embodiments of the surgical tool, will be better understood when read in conjunction with the appended drawings of exemplary embodiments. It should be understood, however, that the invention is not limited to the precise arrangements and instrumentalities shown.

DETAILED DESCRIPTION OF THE EXEMPLARY EMBODIMENTS OF THE INVENTION

Figure 1:
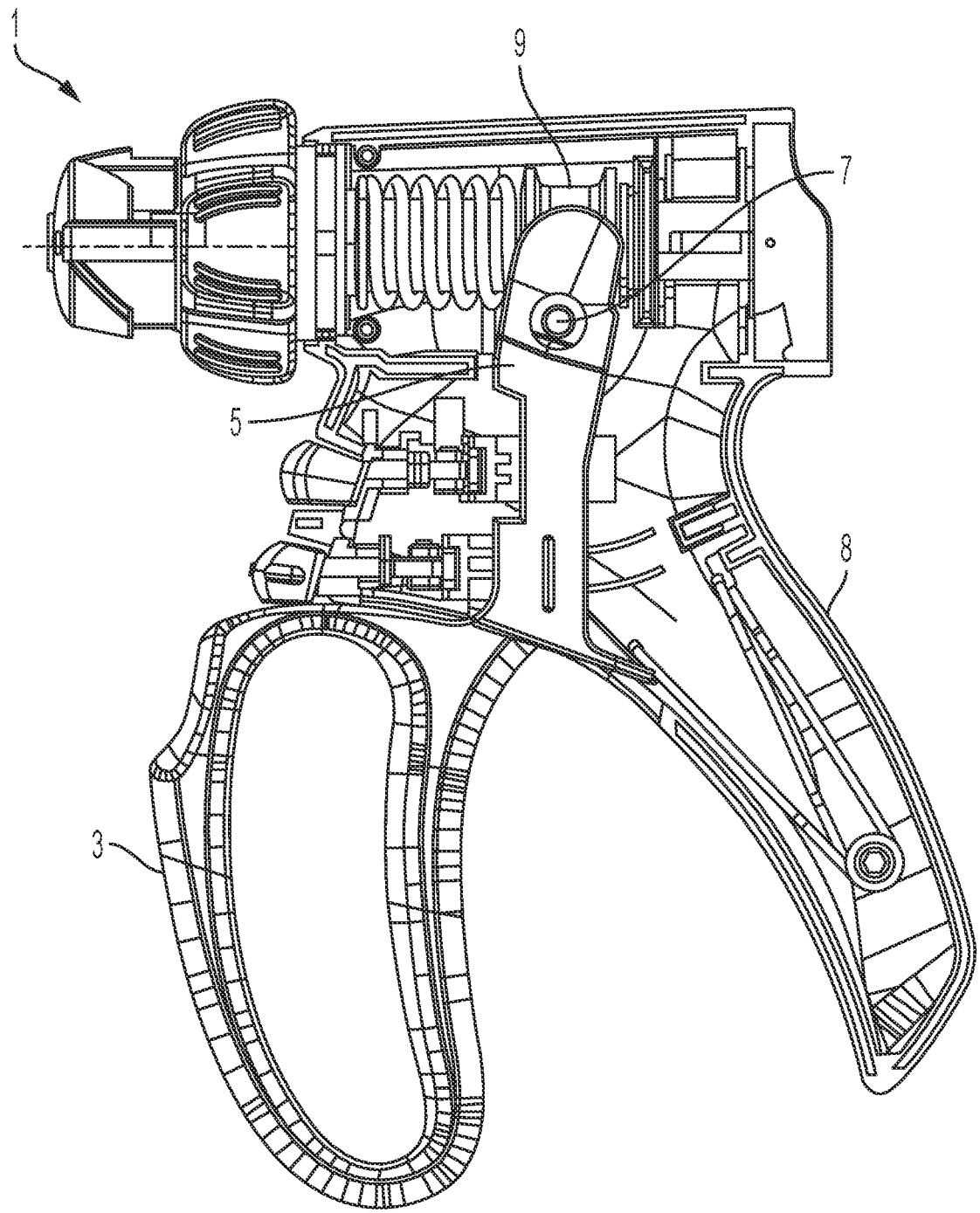
FIG. 1 is a partial cross-sectional view of a prior art open jaw surgical tool.
Figure 2:
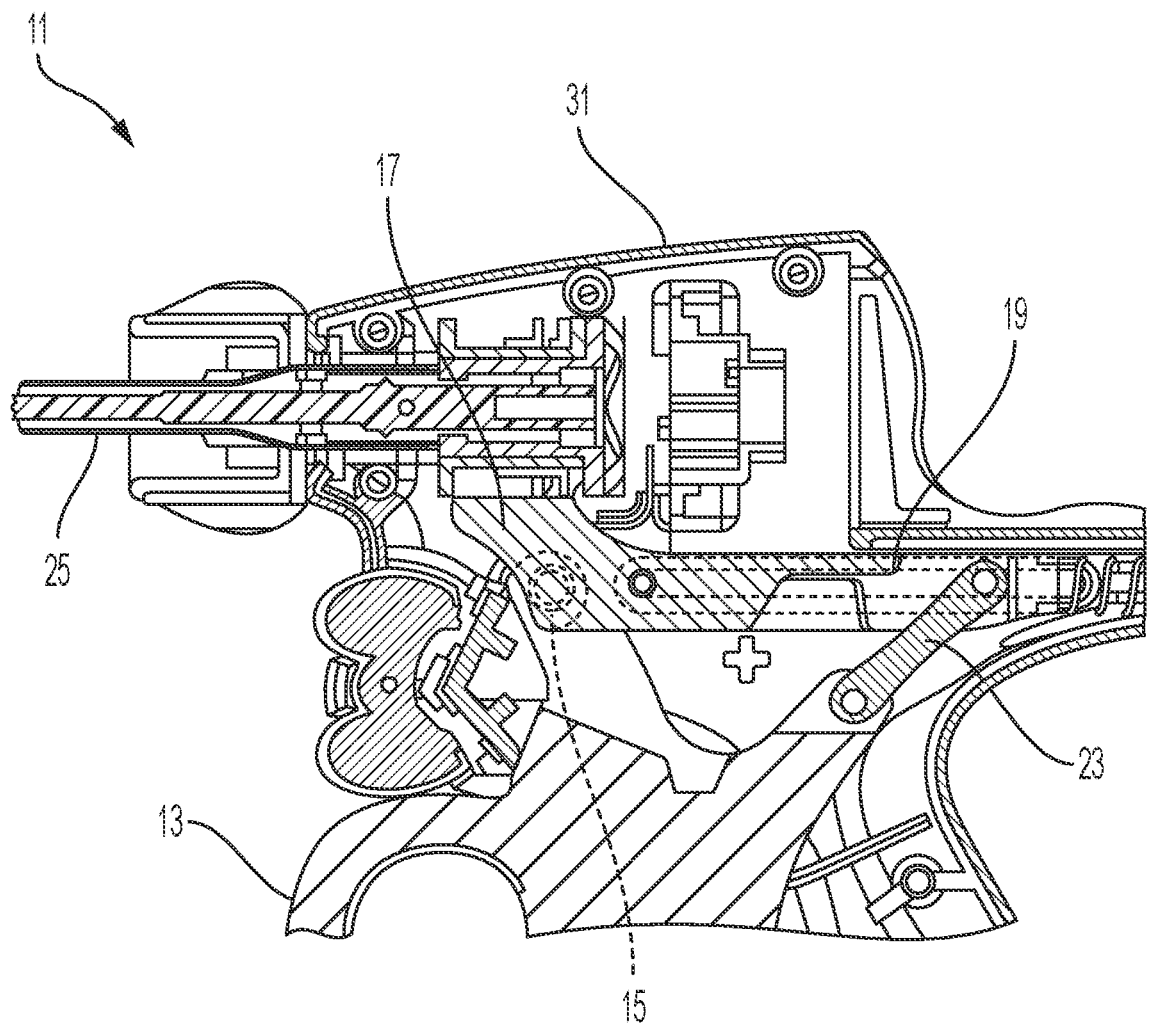
FIG. 2 is a side view of some interior components of another prior art surgical tool.

Referring to FIGS. 1-2, existing surgical tools for laparoscopic procedures include handles that actuate a yoke to perform specific functions, such as actuating a grasping instrument, based on movement of the yoke. The grasping instrument may be disposed at the end of the surgical tool. These surgical tools may be hand-held tools configured to grasp and cut tissue.

As shown in FIG. 1, a known surgical tool 1 may include handle 3, coupling member 5, pivot point 7, grip 8, and slider 9. In some embodiments, surgical tool 1 is configured grasp tissue and/or cut tissue using handle 3 and a grasping instrument (not shown). In some embodiments, grip 8 is configured to be held in the hand of a user (e.g., surgeon or other operator), and a handle 3 is movable relative to grip 8. Handle 3 may be coupled to pivot point 7 via coupling member 5. Handle 3 may be actuated by a user and configured to pivot about pivot point 7 to move slider 9. For example, handle 3 may be coupled to slider 9 and may be actuated by a user such that moving handle 3 results in movement of slider 9. Movement of slider 9 may actuate the grasping instrument disposed at the distal end of surgical tool 1. Grasping instrument may be configured to open and close by actuation of handle 3 relative to grip 8. In some embodiments, the grasping force required to fully actuate handle 3 is large. For example, the gripping force required to fully actuate handle 3 and move slider 9 may be greater than 30 Newtons (N).

As shown in FIG. 2, a known surgical tool 11 may include housing 31, handle 13, link 23, yoke 17, and guide rail 19. Handle 13 may be coupled to housing 31 at pivot point 15. Handle 13 may also be coupled to yoke 17 via link 23 and guide rail 19. Link 23 may be coupled to handle 13 at one end and disposed within guide rail 19 at another end. Link 23 may be configured to slide within guide rail 19, which may result in movement of yoke 17. Similar to surgical tool 1, surgical tool 11 may be a hand-held surgical tool configured to actuate a grasping instrument. For example, in use, a user may apply a gripping force to handle 13. The gripping force on handle 13 is then translated to movement of the grasping instrument disposed at a distal end of surgical tool 11. In some embodiments, surgical tool 11 is configured grasp tissue and/or cut tissue using handle 13 and the grasping instrument. In some embodiments, actuating of handle 13 results in link 23 sliding within guide rail 19, which is coupled to yoke 17, thereby moving yoke 17. Yoke 17 may be attached to a grasper assembly (not shown) or another tool disposed at the end of shaft 25. For example, the grasping force required to fully actuate handle 13 and move yoke 17 may be greater than 30 N. In some embodiments, link 23 and guide rail 19 require significant space within housing 31.

Referring to FIGS. 3A-8, there is shown tool 100 having an improved guide assembly for translating a gripping force applied to a handle to actuation of an end instrument, such as a grasping instrument as shown. In use, tool 100 may be used to actuate an instrument disposed on the tool. The improved guide assembly of tool 100 may better translate the gripping force applied to the handle to actuate the instrument. For example, the improved guide assembly may require a reduced gripping force on the handle of tool 100 to cause actuation of the instrument compared to known surgical tools. Tool 100 may be configured to better translate movement of the handle to movement of the instrument. In some embodiments, tool 100 is configured to translate squeezing (e.g., pivoting) of a handle to axial movement of a yoke, which is coupled to the instrument. Movement of the yoke may result in actuation of the instrument.

In some embodiments, tool 100 is a surgical tool used for grasping, manipulating, and cutting tissue. For example, tool 100 may be a surgical energy device having a grasping instrument configured to grasp, manipulate, and cut/cauterize tissue. The grasping instrument may be coupled to an elongated narrow shaft extending from the housing of tool 100 and may be configured to be inserted within a patient, while a substantial portion of the housing of tool 100 remains outside the patient. The shaft of the open jaw may be inserted within the patient and the elongated shaft may include the grasping instrument that is configured to open and close to grasp tissue.

In some embodiments, tool 100 is configured to grasp and/or cut tissue disposed within small, confined areas. For example, movements of the user's hand on the handle may be translated into corresponding movements of the grasping instrument when used during surgery. In some embodiments, tool 100 is a laparoscopic tool used to grasp and cut tissue during a laparoscopic procedure. However, tool 100 may be a surgical tool used for open surgeries, robotic surgeries, or minimally invasive surgeries. Tool 100 may also be used for non-surgical applications. For example, tool 100 may be used in applications such as automotive, construction, cleaning, manufacturing, non-surgical medical procedures, or any other application desired. Tool 100 may be used for any application requiring translation of a force applied to a handle to actuation of an instrument. In some embodiments, tool 100 is configured to be hand-held by a user.

Figure 3A:
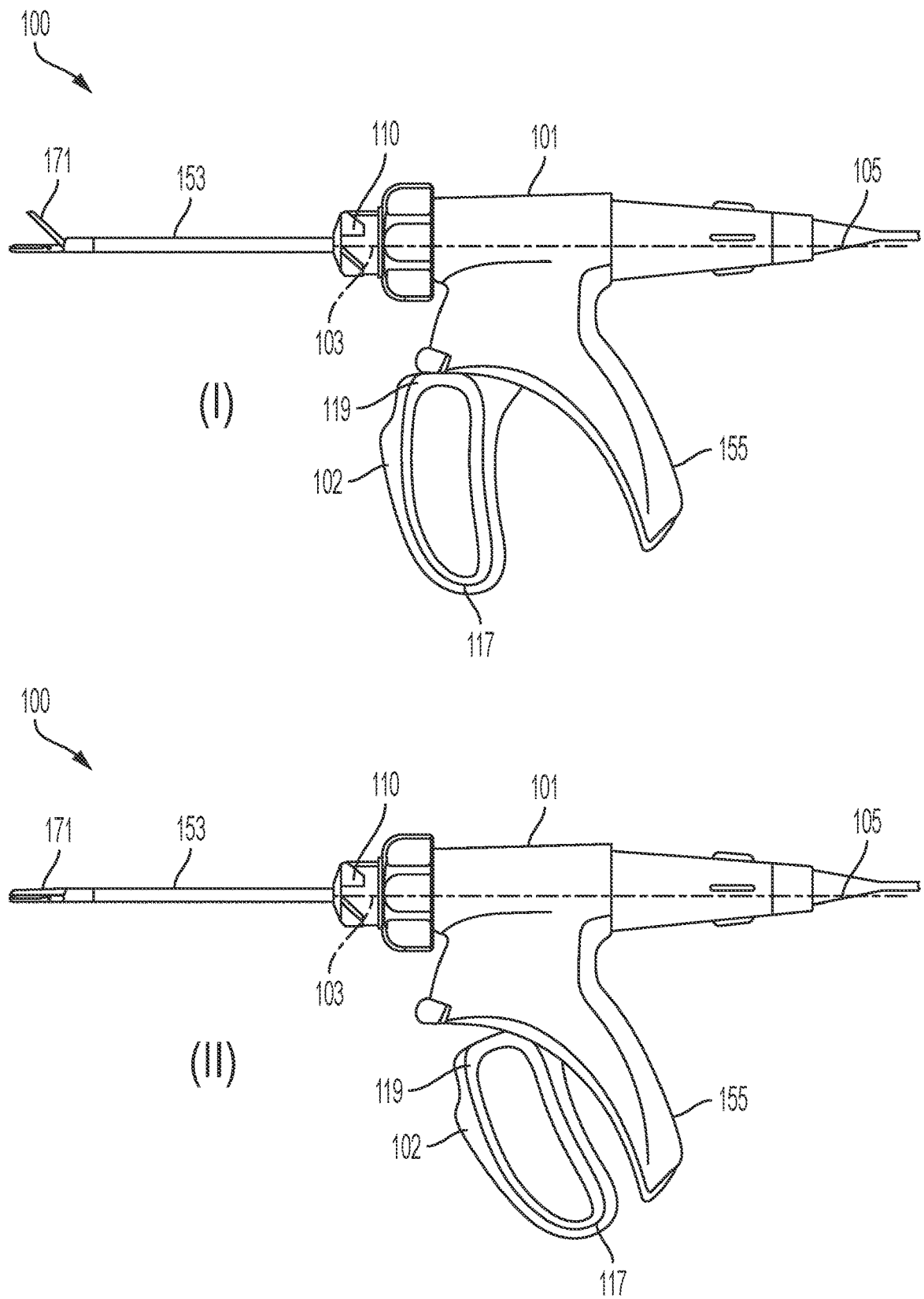
FIG. 3A is a side view of a laparoscopic surgical tool having a grasping instrument in accordance with an exemplary embodiment of the present invention and in which view 3A(I) illustrates the handle in the not grasping or open position and view 3A(II) illustrates the handle in the grasping or closed position.
Figure 3B:
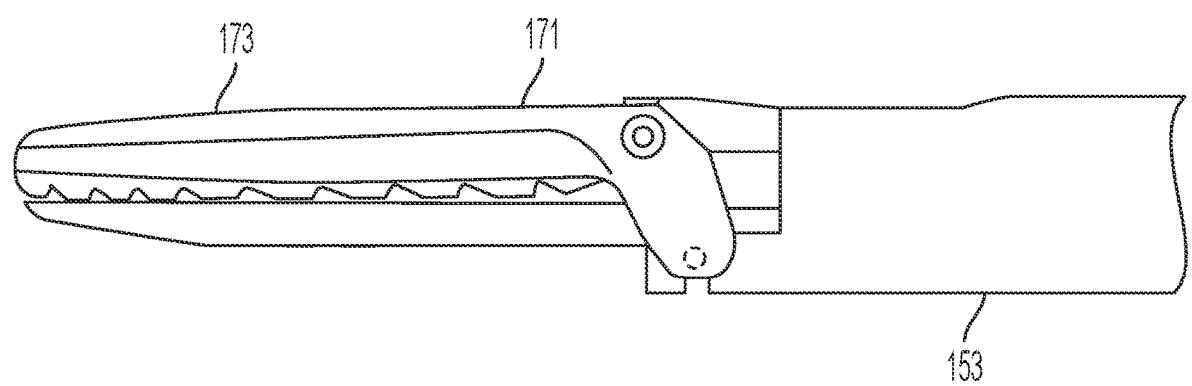
FIG. 3B is zoomed-in view of the grasping instrument of FIG. 3A shown in a closed configuration.
Figure 3C:
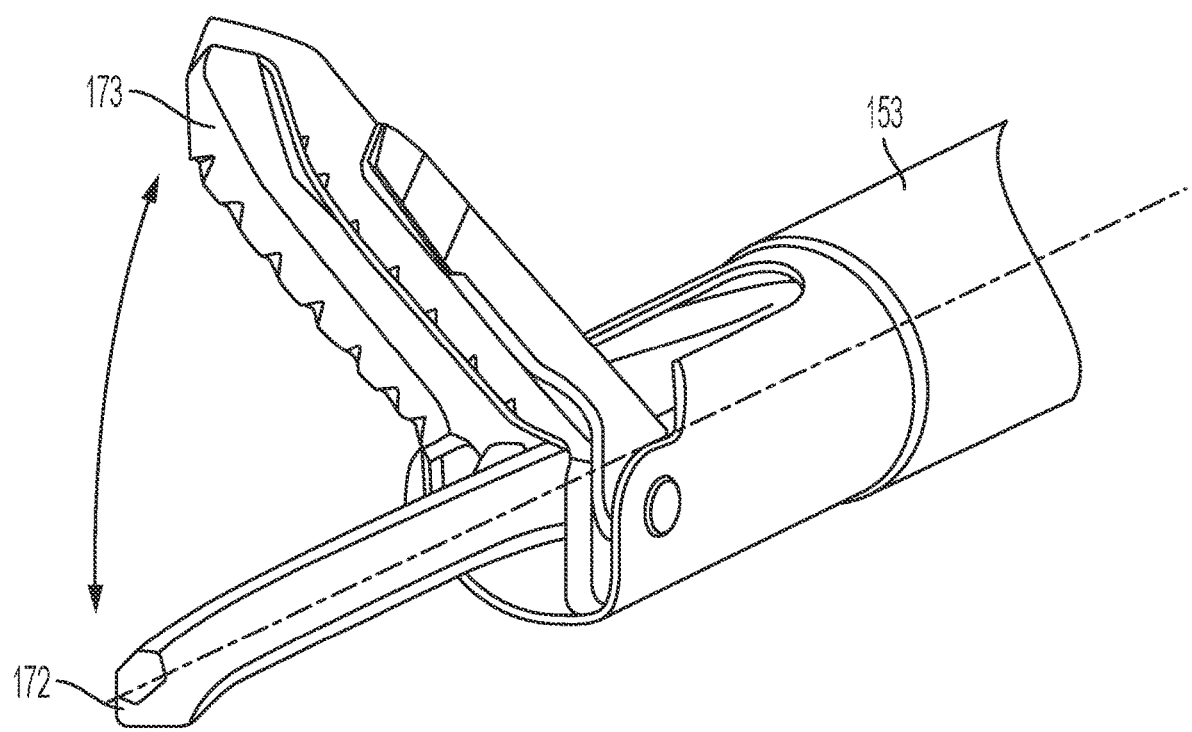
FIG. 3C is zoomed-in view of the grasping instrument of FIG. 3A in an open configuration.

Referring to FIGS. 3A-3C, tool 100 may include housing 101, handle 102, shaft 153, grip 155, and instrument assembly 171. Handle 102 may be actuated by a user to actuate instrument assembly 171. For example, handle 102 may have an initial position (see view (I) in FIG. 3A) and an actuated position (see view (II) in FIG. 3A). The actuated position may be when handle 102 moved relative to grip 155 such that handle 102 is proximate to grip 155 compared to when handle 102 is in the initial position. In use, a user may hold tool 100 by placing grip 155 within their palm and placing their thumb around grip 155. The user's fingers may be wrapped around handle 102 and the user may squeeze their hand, bring their fingers towards their palm and thumb, to pull handle 102 towards grip 155 to actuate handle 102. Actuation of handle 102 may actuate instrument assembly 171. In some embodiments, handle 102 includes a loop and the user's fingers are disposed through the loop during use. However, handle 102 may include no loop, an open loop, finger loops for each finger, a lever, or a trigger to be actuated by a one or more fingers.

In some embodiments, handle 102 is biased to be in the initial position and must be moved by a user or motor to the actuated position. Moving handle 102 to the actuated position may result in actuation of instrument assembly 171. In some embodiments, instrument assembly 171 is a grasping/open jaw instrument and includes a closed (FIG. 3B) and open (FIG. 3C) configuration.

Referring to FIG. 3A, housing 101 may include proximal end 105 and distal end 103. In some embodiments, housing includes longitudinal axis 110 that extends from proximal end 105 through distal end 103 and down shaft 153. Shaft 153 may extend from distal end 103 of housing 101 and instrument assembly 171 may be located at a distal end of shaft 153. In some embodiments, instrument assembly 171 is a grasping instrument. For example, instrument assembly 171 may include jaw 173 and blade 172. Jaw 173 may be movable relative to blade 172 between a closed configuration (FIG. 3B) and an open configuration (FIG. 3C). Blade 172 may be configured to cut and/or cauterize tissue disposed within instrument assembly 171. For example, jaw 173 may be configured to grasp tissue or a vessel and blade 172 may be configured to cut and/or cauterize the tissue or vessel. Blade 172 may be configured to receive electrical current such that it heats up to cauterize tissue. In some embodiments, instrument assembly 171 includes scissors, forceps, needle drivers, retractors, syringes, tubing for suction and/or irrigation, blades/knifes, and/or cauterizing or energy instruments. However, instrument assembly 171 may be any instrument desired. For example, instrument assembly 171 may be an instrument used for medical, automotive, construction, cleaning, manufacturing, or any other application desired.

As shown in FIGS. 4A-8, tool 100 may include handle 102, yoke 106, and guide assembly 115. Yoke 106 and guide assembly 115 may be disposed within housing 101. For example, yoke 106 and guide assembly 115 may be coupled to housing 101. In some embodiments, handle 102 is coupled to housing 101. Handle 102 may be additionally coupled to housing 101 and yoke 106 via guide assembly 115. In some embodiments, housing 101 and yoke 106 are disposed along longitudinal axis 110 and between proximal end 105 and distal end 103. Yoke 106 may be disposed along longitudinal axis 110 and axially aligned with shaft 153. In some embodiments, yoke 106 is coupled to instrument assembly 171 via shaft 153 such that movement of yoke 106 along longitudinal axis 110 causes actuation of instrument assembly 171.

In some embodiments, yoke 106 is coupled to housing 101 to allow yoke 106 to move axially along longitudinal axis 110. For example, yoke 106 may be slidably coupled to housing 101 such that yoke 106 is configured to move along longitudinal axis 110 from proximal end 105 to distal end 103. Yoke 106 may also be configured to move axially in alignment with shaft 153. In some embodiments, yoke 106 is coupled to housing 101 along a track to allow yoke 106 to move axially along longitudinal axis 110. However, yoke 106 may be coupled to housing 101 via other methods, such as via magnets, rails, wheels, biasing elements, springs, tension members, or any other method desired. Movement of yoke 106 along longitudinal axis 110 may result in actuation of instrument assembly 171.

In some embodiments, yoke 106 includes protrusion 109 and housing 101 includes inside track 111 and an outside track (not shown). Inside track 111 may be configured to receive protrusion 109 such that yoke 106 is slidable relative to housing 101. For example, yoke 106 may be slidable along inside track 111 and/or the outside track such that yoke 106 is slidable along longitudinal axis 110 relative to housing 101. In some embodiments, protrusion 109 is configured to rest on inside track 111 and/or the outside track such that protrusion 109 and yoke 106 is slidable along one or more of inside track 111 or the outside track. In some embodiments, inside track 111 includes stopping portion 113 to prevent yoke 106 from moving too far back towards proximal end 105. Inside track 111 and/or the outside track may be configured to allow yoke 106 to move along longitudinal axis 110 from distal end 103 to proximal end 105.

In some embodiments, handle 102 is coupled and secured to housing 101. Handle 102 may be configured to move from the initial position to the actuated position. The actuated position may be when handle 102 is proximate proximal end 105 compared to when handle 102 is in the initial position. In some embodiments, the initial position of handle 102 is when handle 102 has not been actuated by a user. The initial position of handle 102 may be when handle 102 is at rest and yoke 106 is disposed proximate proximal end 105 compared to when handle 102 is actuated. In some embodiments, the force required to move handle 102 from the initial position to the actuated position is approximately 30 N or less. For example, the force required to move handle 102 from the initial position to the actuated position may be less than 35 N. In some embodiments, the axial force required to move handle 102 from the initial position to the actuated position is approximately 150 N or less. The axial force may be the force that is applied along longitudinal axis 110. For example, the axial force may be the force the drives yoke 106 from proximal end 105 to distal end 103. In some embodiments, the axial force drives yoke 106 along longitudinal axis 110. In other words, the axial force is the force transmitted through shaft 153 to actuate instrument assembly 171, such as jaw 173. In some embodiments, when an axial force is transmitted to jaw 173 via yoke 106, jaw 173 rotates around a pivot point connected to shaft 153 resulting in jaw 173 closing. The direction of the axial force coincides with the direction of shaft 153.

Figure 4A:
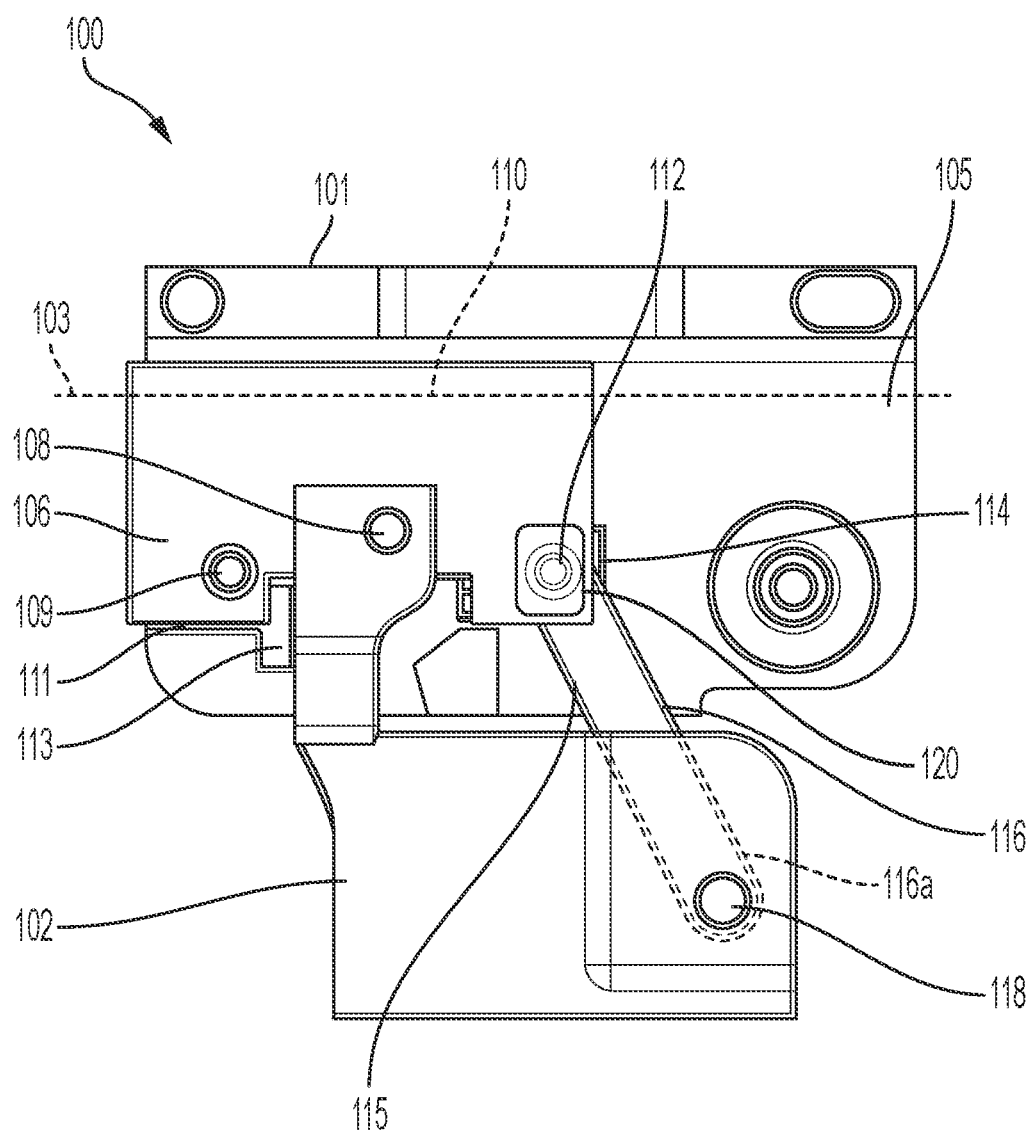
FIG. 4A is a partial side view of the guide assembly of the surgical tool of FIG. 3A with the housing and handle removed for demonstrative purposes.

Referring to FIG. 4A, handle 102 may be pivotally coupled to housing 101. In some embodiments, handle 102 is coupled to housing 101 via pivot point 108. For example, handle 102 may be configured to rotate or pivot about pivot point 108. In some embodiments, when handle 102 moves from the initial position to the actuated position, handle 102 pivots towards distal end 103, and yoke 106 is driven forward towards distal end 103 of housing 101 via guide assembly 115.

In some embodiments, driving of yoke 106 results in actuation of instrument assembly 171. For example, instrument assembly 171 may be coupled to yoke 106 via shaft 153. In some embodiments, driving of yoke 106 proximally and distally causes jaw 173 of instrument assembly 171 to open and close. For example, moving handle 102 from the initial position to the actuated position may result in driving yoke 106 towards distal end 103 thereby causing jaw 173 to close. Movement of handle 102 from the actuated position back to the initial position may cause yoke 106 to move proximally, causing jaw 173 to open. However, instrument assembly 171 may be any instrument desired such that movement of handle 102 and yoke 106 causes actuation of instrument assembly 171.

In some embodiments, handle 102 and yoke 106 may each have a stroke length. The stroke length may be the length of the movement required to fully actuate handle 102 or full length of movement of yoke 106. In some embodiments, handle 102 may have a stroke length between approximately 5 mm and approximately 25 mm. In a preferred embodiment, handle 102 has a stroke length between 9 mm and 14 mm. In some embodiments, yoke 106 may have a stroke length between approximately 1 mm and approximately 20 mm. In a preferred embodiment, yoke 106 has a stroke length between approximately 3 mm and approximately 5 mm.

In some embodiments, handle 102 is coupled to yoke 106 via guide assembly 115. Guide assembly 115 may be configured to drive yoke 106 proximally and distally upon movement of handle 102. Guide assembly 115 may be sized and shaped to be entirely disposed within housing 101. For example, guide assembly 115 may not extend into grip 155 and may have a maximum length of less than or equal to 40 mm. In some embodiments, guide assembly 115 is sized to occupy less than 3200 $mm^3$ within housing 101.

Figure 4B:
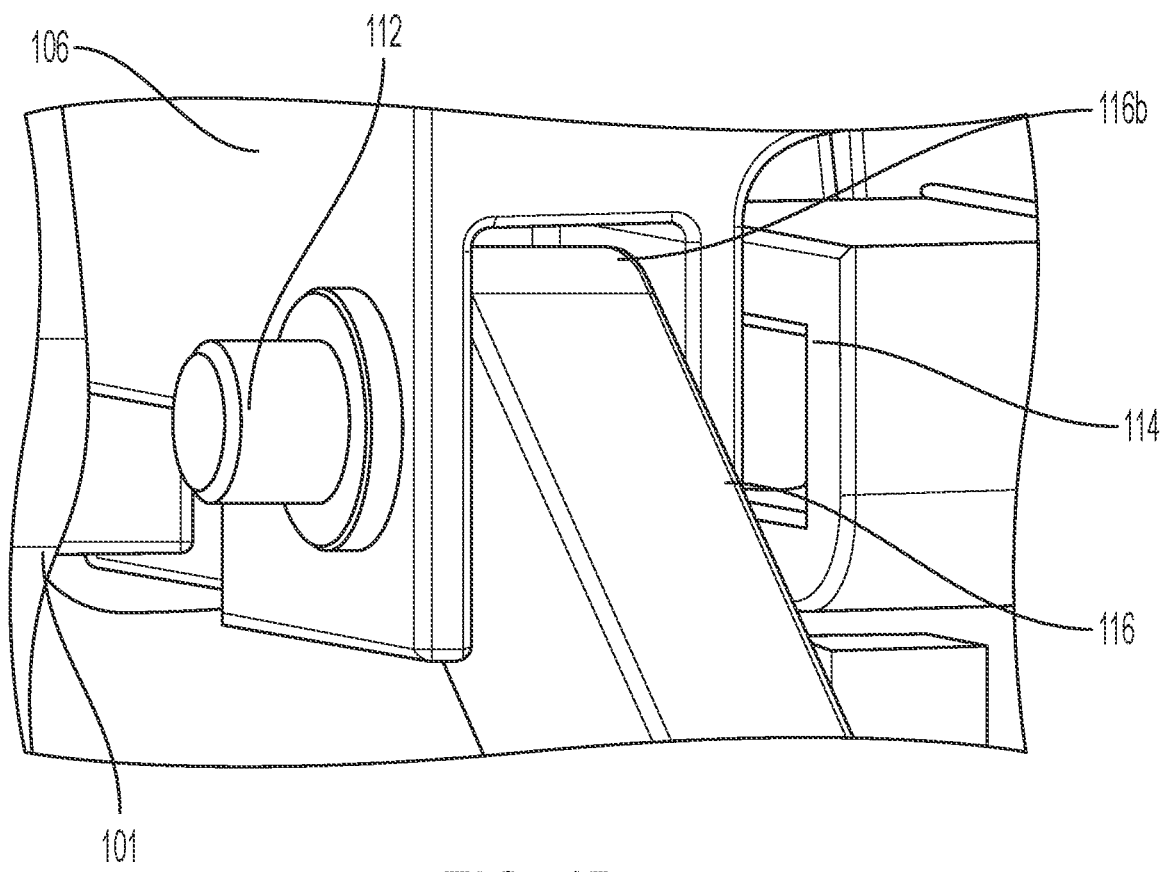
FIG. 4B is a partial perspective view of the guide assembly of FIG. 4A.

Referring to FIGS. 4A-4B, guide assembly 115 may include link 116 and guide rail 114. Link 116 may be configured to slide within guide rail 114 during actuation of handle 102. For example, guide rail 114 may be disposed within housing 101 and when handle 102 moves from the initial position to the actuated position, link 116 may slide along guide rail 114. Due to link 116 being coupled to yoke 106, when link 116 slides along guide rail 114, link 116 may drive yoke 106 towards distal end 103. In some embodiments, upon actuation, of handle 102, link 116 is driven upwards and towards distal end 103 along guide rail 114, thereby driving yoke 106 and actuating instrument assembly 171. Link 116 may couple handle 102 to yoke 106 such that actuation of handle 102 drives link 116 towards distal end 103, thereby driving yoke 106 towards distal end 103. Yoke 106 driving towards distal end 103 may actuate instrument assembly 171. Link 116 may have first end 116a and second end 116b. First end 116a of link 116 may be coupled to handle 102. In some embodiments, first end 116a is rotatably coupled to handle 102. First end 116a may be coupled to handle 102 via first pivot pin (handle pivot pin) 118. First end 116a may be coupled to handle 102 such that first end 116a is fixed in location relative to handle 102 and is only configured to pivot about first pivot pin 118. Second end 116b of link 116 may be pivotably coupled to yoke 106 at second pivot pin (yoke pivot pin) 112.

In some embodiments, second pivot pin 112 is configured to move relative to housing 101. For example, second pivot pin 112 may be configured to move proximally and distally and away and towards handle 102. Second pivot pin 112 being movable relative to housing 101 results in second end 116b of link 116 being movable relative to housing 101. In some embodiments, second pivot pin 112 extends through yoke 106. For example, second pivot pin 112 may extend through the width of yoke 106. In some embodiments, first pivot pin 118 is disposed lower than second pivot pin 112. In some embodiments, first pivot pin 118 and second pivot pin 112 are disposed below pivot point 108.

Referring to FIGS. 3A and 4A, first pivot pin 118 may extend through handle 102 and second pivot pin 112 may extend through yoke 106 and/or housing 101. For example, second pivot pin 112 may extend through the width of yoke 106 and/or the width of housing 101. In some embodiments, handle 102 may be coupled to housing 101 via pivot point 108, which may be disposed higher than both first pivot pin 118 and second pivot pin 112. For example, handle 102 may include top 119 and bottom 117. One or more of first pivot pin 118 and second pivot pin 112 may be disposed closer to bottom 117 than pivot point 108. For example, pivot point 108 may be disposed higher than one or more of first pivot pin 118 and/or second pivot pin 112 resulting in one or more of first pivot pin 118 and/or second pivot pin 112 being disposed closer to bottom 117 of handle 102 compared to pivot point 108. In some embodiments, second pivot pin 112 is disposed closer to bottom 117 than first pivot pin 118. First pivot pin 118 may be disposed closer to bottom 117 than pivot point 108.

In some embodiments, second pivot pin 112 may be disposed lower than pivot point 108 and closer to bottom 117, such that pivot point 108 is higher than second pivot pin 112. Pivot point 108 being disposed higher than second pivot pin 112 may result in the distance between the gripping force applied to handle 102 and pivot point 108 being greater than the distance between the gripping force applied to handle 102 and second pivot pin 112. In some embodiments, placing pivot point 108 higher than second pivot pin 112 results in a reduction in the gripping force required to actuate handle 102. In practice, placing pivot point 108 above second pivot pin 112 changes the direction that handle 102 is moved compared to existing conventional surgical tools, thereby reducing the force required to actuate handle 102. In some embodiments, first pivot pin 118 and second pivot pin 112 are disposed below pivot point 108. In some embodiments, pivot point 108 overlaps with yoke 106. For example, pivot point 108 may be adjacent to yoke 106 such that pivot point 108 overlaps with yoke 106 and first pivot pin 118 may not.

Referring to FIGS. 4A and 4B, link 116 may have a length greater than its width. Link 116 may have a length between approximately 10 mm and approximately 100 mm and a width of between approximately 5 mm and 50 mm. In some embodiments, link 116 has a width of approximately 10 mm. In a preferred embodiment, link 116 has a length between approximately 20 mm and approximately 40 mm. In some embodiments, link 116 is substantially rigid and comprised of polycarbonate or polyacetal. Link 116 may be sized and shaped to fit within a small confined area of housing 101, thereby reducing the amount of space required for guide assembly 115.

In some embodiments, guide assembly 115 includes first pivot pin 118 and second pivot pin 112. First pivot pin 118 may have a diameter of approximately 4 mm and second pivot pin 112 may have a diameter of approximately 4 mm. However, first pivot pin 118 and second pivot pin 112 may have a diameter between approximately 1 mm and approximately 10 mm. In some embodiments, first pivot pin 118 and second pivot pin 112 each have a different diameter. Each of first pivot pin 118 and second pivot pin 112 may be received through housing 101 via apertures disposed within housing 101. In some embodiments, each of first pivot pin 118 and second pivot pin 112 extends through a substantial width of housing 101.

In some embodiments, second pivot pin 112 may extend through yoke 106, link 116, and guide rail 114. Second pivot pin 112 may be slidably disposed through guide rail 114 such that second pivot pin 112 can slide within and along guide rail 114. In some embodiments, second pivot pin 112 is disposed through a portion of yoke 106, then through link 116, then another portion of yoke 106 before extending through guide rail 114 and out of housing 101. Guide rail 114 may be configured to limit the movement of second pivot pin 112, thereby limiting the movement of second end 116b of link 116 and thus yoke 106. For example, guide rail 114 may provide a specific path for second pivot pin 112, and thus second end 116b of link 116, to travel along. Guide rail 114 may have a length dependent on the stroke length of yoke 106. For example, in embodiments where yoke 106 has a long stroke length, guide rail 114 may be longer than in embodiments where yoke 106 has a shorter stroke length. In some embodiments, guide rail 114 has a length longer than the stroke length of yoke 106. For example, yoke 106 may have a stroke length of approximately 4 mm, which may result in guide rail 114 having a length of approximately 5 mm or greater.

In some embodiments, movement of handle 102 from the initial position to the actuated position drives first pivot pin 118 upwards resulting in first end 116a of link driving upwards towards yoke 106. First end 116a of link 116 driving upwards results in second end 116b of link 116 pivoting about second pivot pin 112 and pushing forward towards distal end 103. Second pivot pin 112 may push forward toward distal end 103 as it slides along guide rail 114 and may drive yoke 106 towards distal end 103 since second pivot pin 112 couples link 116 to yoke 106. In some embodiments, the force applied to handle 102 may be transmitted along link 116 to drive yoke 106 towards distal end 103.

Figure 5A:
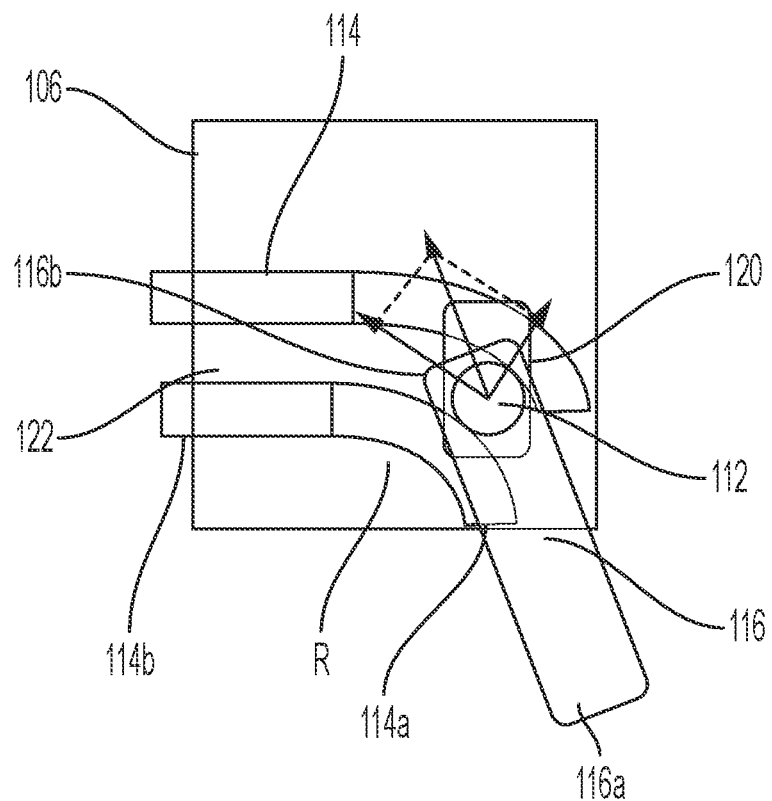
FIG. 5A is a partial cross-sectional side view of the guide assembly of the surgical tool of FIG. 3A shown in an initial position.
Figure 5B:
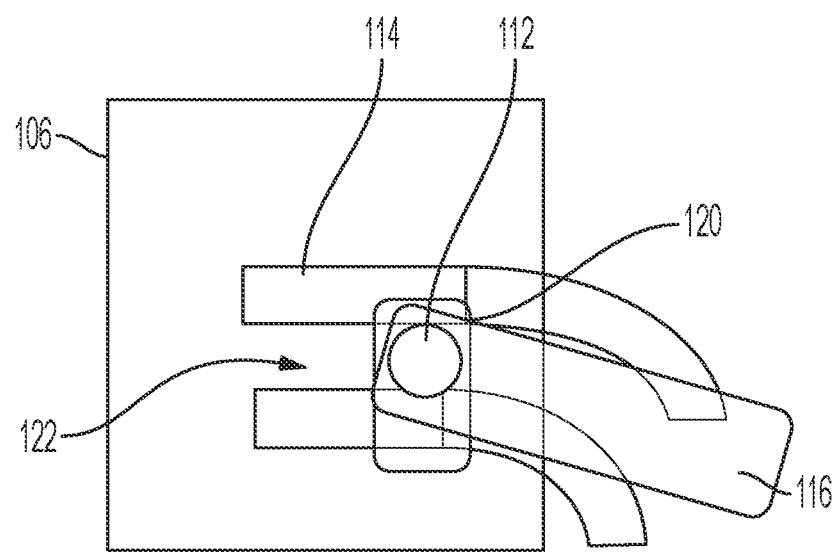
FIG. 5B is a partial cross-sectional side view of the guide assembly of FIG. 4A shown in an actuated position.

Referring to FIGS. 5A-5B, guide assembly 115 may include guide rail 114. Guide rail 114 may extend through housing 101 and may include channel 122, which may be disposed within guide rail 114. In some embodiments, second pivot pin 112 moves and slides within channel 122. In some embodiments, guide rail 114 is curved. Guide rail 114 may include a non-curved portion and a curved portion. In some embodiments, the curved portion has a length of approximately 2 mm and the non-curved portion has a length of approximately 3 mm. However, the curved portion may have a length between approximately 1 mm and approximately 10 mm and the non-curved portion may have a length between approximately 1 mm and approximately 10 mm. In one embodiment, the curved portion of guide rail 114 has a length greater than a length of the non-curved portion of guide rail 114. In another embodiment, the curved portion of guide rail 114 has a length less than a length of the non-curved portion of guide rail 114. In yet another embodiment, the curved portion of guide rail 114 has a length substantially equal to a length of the non-curved portion of guide rail 114. The curved portion may be proximate proximal end 105 compared to the non-curved portion. For example, a portion of guide rail 114 proximate proximal end 105 may be curved downwards thus disposed lower than a portion of guide rail 114 proximate distal end 103. In some embodiments, a portion of guide rail 114 proximate proximal end 105 is disposed closer to first pivot pin 118 than a portion of guide rail 114 proximate distal end 103.

In some embodiments, guide rail 114 being curved reduces the contact angle between second pivot pin 112 and guide rail 114, thereby reducing the frictional force between second pivot pin 112 and guide rail 114. For example, as handle 102 is actuated, second pivot pin 112 may slide along channel 122 of guide rail 114, which results in a frictional force between second pivot pin 112 and guide rail 114. Guide rail 114 being curved reduces the frictional force between second pivot pin 112 and guide rail 114 when second pivot pin 112 slides along guide rail 114 compared to guide rail 114 being non-curved. Reducing the frictional force between second pivot pin 112 and guide rail 114 results in less of a gripping force needed to actuate handle 102. For example, a decrease in the frictional force between second pivot pin 112 and guide rail 114 results in less of a frictional force needing to be overcome to drive yoke 106, and thus less of a gripping force to actuate handle 102. In other words, reducing the frictional force between second pivot pin 112 and guide rail 114 results in less of a force needing to be overcome to allow for actuation of handle 102 to drive yoke 106.

In some embodiments, guide rail 114 being curved downward towards handle 102 results in an increase in the force efficiency when handle 102 is moved from the initial position to the actuated position. For example, when guide rail 114 is curved downward towards proximal end 105, as user actuates handle 102, the gripping force required decreases as handle 102 moves to the actuated position. Guide rail 114 being curved downward towards handle 102 may result in a decrease in gripping force required to keep handle 102 in the actuated position compared to guide rail 114 not being curved downward. In some embodiments, guide rail 114 curving downward towards handle 102 may minimize the amount of space that guide assembly 115 occupies. For example, guide rail 114 being linear instead of curved would result in guide assembly 115 occupying significant more space within housing 101.

Guide rail 114 may include proximal end 114a and distal end 114b. In some embodiments, proximal end 114a may be disposed below distal end 114b, such that proximal end 114a is disposed closer to handle 102 than distal end 114b. Proximal end 114a may be disposed lower than distal end 114b due to guide rail 114 being curved downwards towards handle 102 at proximal end 114a. In some embodiments, guide rail 114 is curved and has radius of curvature R. Radius of curvature R may be 10 mm.

In some embodiments, channel 122 is disposed between proximal end 114a and distal end 114b. Channel 122 may be sized and shaped such that second pivot pin 112 is slidable within channel 122. For example, second pivot pin 112 may be configured to slide between proximal end 114a and distal end 114b of guide rail 114 within channel 122. Channel 122 may be sized and shaped to extend through guide rail 114 and receive a portion of second pivot pin 112. Channel 122 may have a width greater than the diameter of second pivot pin 112. In some embodiments, channel 122 has a width slightly larger than the diameter of second pivot pin 112. In some embodiments, channel 122 has a width between approximately 2 mm and approximately 8 mm. For example, channel 122 may have a width of approximately 4.5 mm. In some embodiments, second pivot pin 112 may slide within channel 122 of guide rail 114. For example, as handle 102 moves from the initial position to the actuated position, second pivot pin 112 may slide in the proximal to distal direction.

Referring to FIGS. 4A and 5A-5B, guide assembly 115 may include guide hole or guide aperture 120. Guide hole 120 may be an aperture that extends through a portion of yoke 106 and may be located on yoke 106 adjacent second end 116b of link 116. In some embodiments, guide hole 120 is rectangular in shape. However, guide hole 120 may be circular, elliptical, oval, triangular, or any shape desired. Guide hole 120 may be sized and shaped to allow second pivot pin 112 to move within guide hole 120. Guide hole 120 may be configured to allow second pivot pin 112 to slide within guide rail 114, thereby moving yoke 106 in the proximally and distally. For example, since guide rail 14 is curved, guide hole 120 may allow for second pivot pin 112 to move vertically within guide hole 120. In practice, as second pivot pin 112 moves from proximal end 114a to distal end 114b, second pivot pin 112 may move upwards distal end 114b is disposed above proximal end 114a. As second pivot pin 112 moves from proximal end 114a to distal end 114b, second pivot pin 112 may move upwards within guide hole 120. Guide hole 120 may have a length greater than its width to allow second pivot pin 112 to slide within channel 122 and drive yoke 106 distally and proximally. Guide hole 120 may be a vertical long hole to allow second pivot pin 112 to slide within channel 122 of guide rail 114 due to guide rail 114 being curved. Guide hole 120 being a vertical long hole may also prevent yoke 106 from moving in the vertical direction when handle 102 moves from the initial position to the actuated position due to second pivot pin 112 driving upwards when sliding distally along guide rail 114. Guide hole 120 may have a length of between approximately 2 mm and approximately 12 mm and a width between approximately 1 mm and approximately 8 mm. In some embodiments, guide hole 120 has a length of approximately 8 mm and a width of approximately 4 mm.

In practice, when handle 102 moves from the initial position (illustrated, for example, in view (I) of FIG. 3A and corresponding partial side view of the guide assembly in FIG. 5A) to the actuated position (illustrated, for example, in view (II) of FIG. 3A and corresponding partial side view of the guide assembly in FIG. 5B), handle 102 pivots about pivot point 108. Handle 102 pivoting about pivot point 108 results in handle 102 driving first pivot pin 118 and first end 116a of link 116 upwards toward housing 101, as well as pivoting about first pivot pin 118. Driving first pivot pin 118 and first end 116a towards housing 101 results in link 116 driving second end 116b up within guide hole 120 and in the distal direction. Second end 116b moving up within guide hole 120 and along guide rail 114 towards distal end 103 results in second pivot pin 112 sliding along channel 122 of guide rail 114, thereby driving yoke 106 towards distal end 103. In some embodiments, guide hole 120 allows second pivot pin 112 to slide within guide rail 114 while driving yoke 106 distally or proximally. In some embodiments, driving yoke 106 towards distal end 103 results in actuating of instrument assembly 171, such as a grasper assembly. In other words, when handle 102 is moved from the initial position to the actuated position, yoke 106 is driven towards distal end 103 via guide assembly 115, which actuates instrument assembly 171.

In some embodiments, tool 100 is used in conjunction with robotic surgical devices for robotic surgeries and includes a motor. The motor may be configured to drive second pivot pin 112. For example, instead of handle 102, a motor may be used to drive link 116 and second pivot pin 112 upwards, thereby driving yoke 106 towards distal end 103. The motor may be coupled to a robotic surgical device and may be controlled by a user. In some embodiments, a user may actuate the motor, which causes movement of second pivot pin 112, thereby driving yoke 106 towards distal end 103 and actuating instrument assembly 171.

Figure 6A:
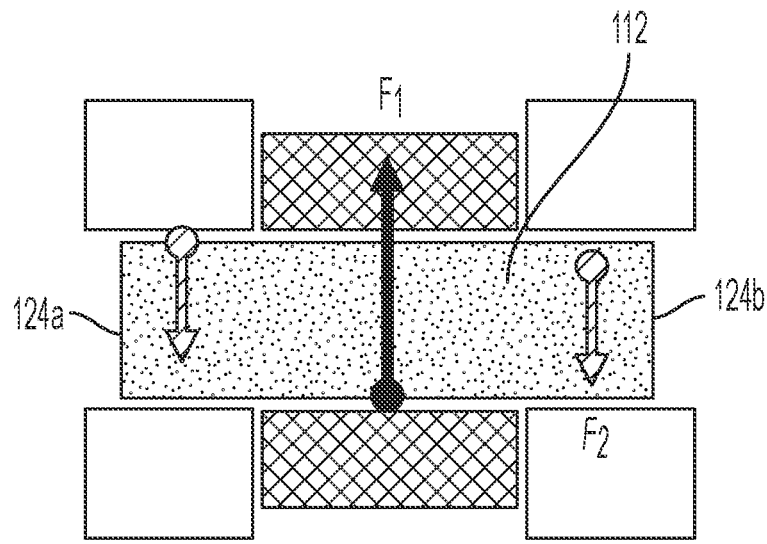
FIG. 6A is a schematic view of an exemplary pivot pin of the surgical tool of FIG. 3A.
Figure 6B:
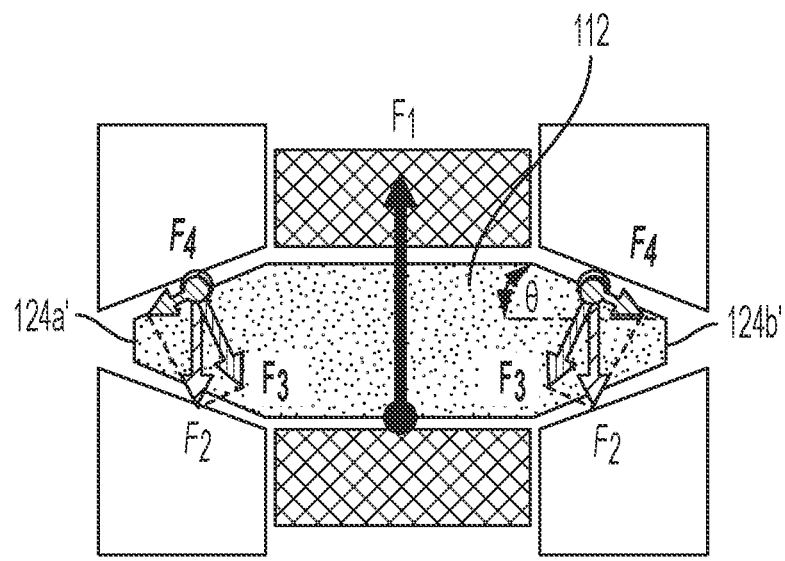
FIG. 6B is a schematic view of an alternative exemplary pivot pin of the surgical tool of FIG. 3A.

Referring to FIGS. 6A and 6B, second pivot pin 112 may have first end 124a and second end 124b. First end 124a and second end 124b may be portions of second pivot pin 112 that contact guide hole 120 and/or guide rail 114. In some embodiments, first end 124a and second end 124b are flat and non-tapered. However, first end 124a and second end 124b being non-tapered may result in considerable frictional force between second pivot pin 112 and guide hole 120 and/or guide rail 114. In some embodiments, to reduce the amount of frictional force between second pivot pin 112 and guide hole 120 and/or guide rail 114, second pivot pin 112 may include first end 124a' and second end 124b', which are tapered. First end 124a' and second end 124b' being tapered decreases the perpendicular force felt on first end 124a' and second end 124b' by guide hole 120 and/or guide rail 114. Further, first end 124a' and second end 124b' being tapered may decrease the frictional force between second pivot pin 112 and guide hole 120 and/or guide rail 114 when second pivot pin 112 slides within guide hole 120 and/or guide rail 114. In some embodiments, second pivot pin 112 may taper from a diameter of approximately 4 mm to a diameter of approximately 2 mm.

Figure 7:
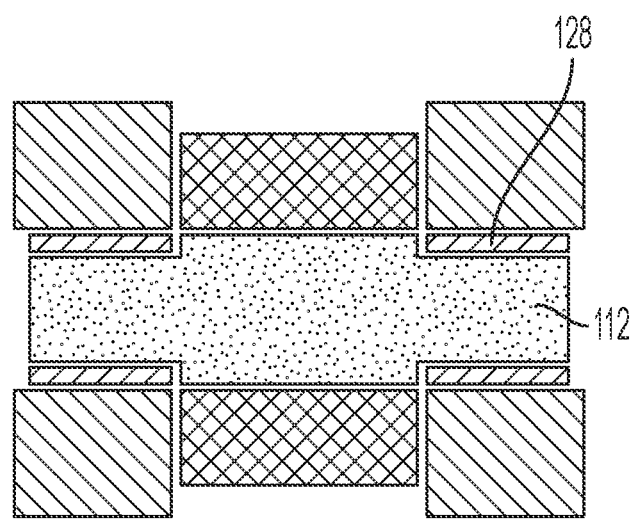
FIG. 7 is a perspective view of an exemplary ring disposed around a pivot pin of the surgical tool of FIG. 3A.

Referring to FIG. 7, second pivot pin 112 may include one or more rings 128. Ring 128 may be a low friction ring disposed around the circumference of second pivot pin 112 to reduce the amount of friction between guide hole 120 and/or guide rail 114 and second pivot pin 112. In some embodiments, second pivot pin 112 may include ring 128 proximate first end 124a or 124a' and/or proximate second end 124b or 124b'. However, second pivot pin 112 may include ring 128 at any location. For example, second pivot pin 112 may include ring 128 across the entire exterior surface or may include ring 128 only where second pivot pin 112 contacts guide hole 120 and/or guide rail 114. In some embodiments, one or more of first pivot pin 118 and second pivot pin 112 includes one or more rings 128.

Figure 8:
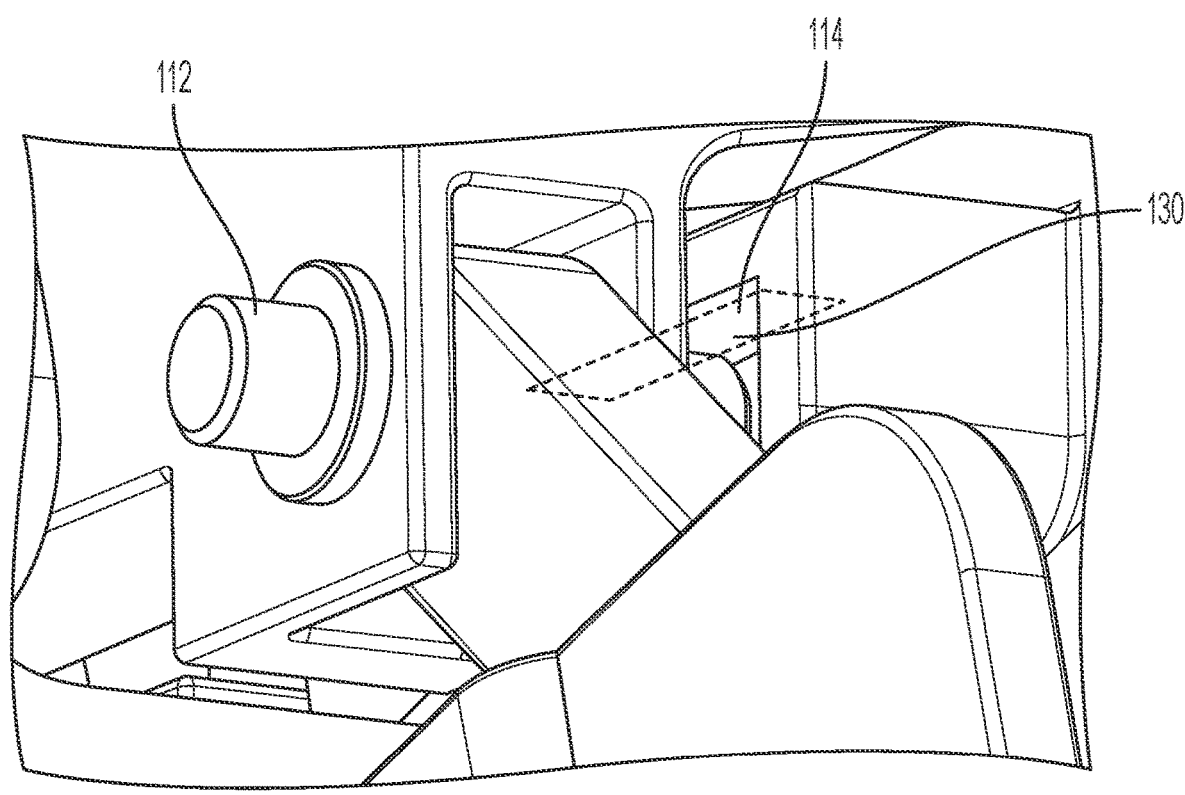
FIG. 8 is a perspective view of the guide assembly of FIG. 3A showing an exemplary low-friction coating applied to a surface contacting a pivot pin.

Referring to FIG. 8, guide hole 120 and/or guide rail 114 may include coating 130, which may be a low-friction coating. Coating 130 may be applied within the interior surface of guide hole 120 and/or guide rail 114. For example, coating 130 may be applied to the portion of guide hole 120 and/or guide rail 114 that contacts second pivot pin 112. Coating 130 may be applied to guide hole 120 and/or guide rail 114 during manufacturing of tool 100. Coating 130 may be a substance that is coated on the interior of guide hole 120 and/or guide rail 114 or may be a material coupled to the interior of guide hole 120 and/or guide rail 114. For example, coating 130 may be a low-friction primer applied to the interior of guide hole 120 and/or guide rail 114 or coating 130 may be a low-friction strip of material coupled to the interior of guide hole 120 and/or guide rail 114 by, for example, an adhesive. Coating 130 may be PTFE coating. Coating 130 may be applied to a portion of guide hole 120 and/or guide rail 114 or the entirety of guide hole 120 and/or guide rail 114. For example, coating 130 may be interspersed within guide hole 120 and/or guide rail 114 or may cover the entirety of guide hole 120 and/or guide rail 114. In some embodiments, coating 130 is applied to any locations where first pivot pin 118 and/or second pivot pin 112 contacts a surface.

Figure 9:
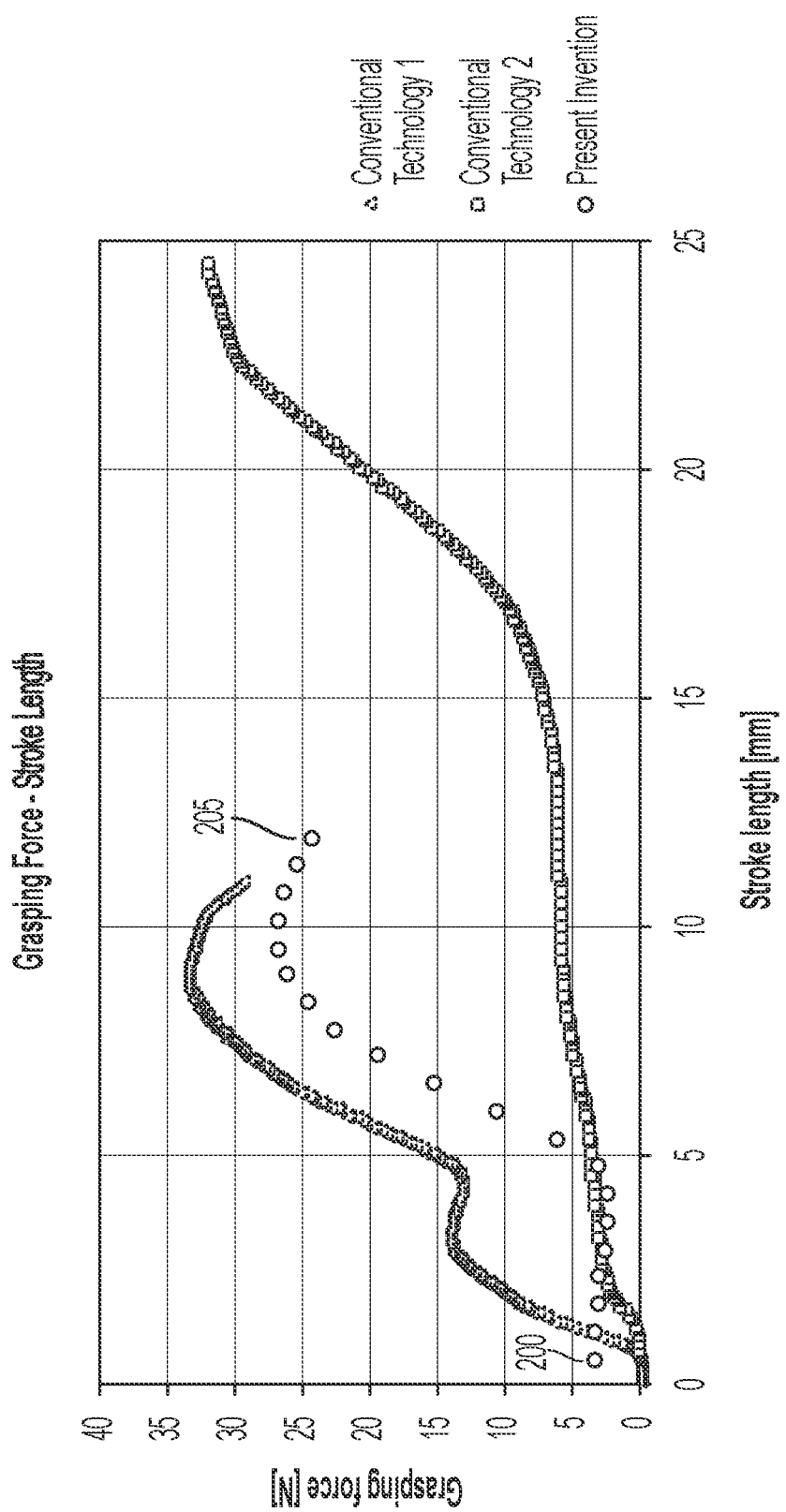
FIG. 9 is a graph illustrating the required actuation grasping force over the stroke length of the handle of an exemplary embodiment of the present invention and the prior art.

Referring to FIG. 9, a graph is provided illustrating the gripping force required to achieve the desired stroke length. For the present invention sample, the graph in FIG. 9 shows the grasping force [N] as the stroke length [mm] changes in the process of handle 102 transitioning from the initial position illustrated in view (I) of FIG. 3A and FIG. 4A (corresponding to location 200 in FIG. 9) to the actuated position illustrated in view (II) of FIG. 3A and FIG. 4B (corresponding to location 205 in FIG. 9). As shown in the graph, tool 100 may require less of a gripping force to reach the desired stroke volume compared to other prior art tools, such as Conventional Technology 1 and Conventional Technology 2. For example, tool 100 allows for the maximum gripping force to actuate handle 102 to be less than 35 N and the stroke length of handle 102 to be less than 14 mm. This results in an approximately 10% decrease in the maximum gripping force required to actuate handle 102 compared to other prior art tools.

In practice, the smaller the gripping force and the shorter the stroke length, the less fatigue a user will experience when using tool 100. Further, users with small hands or weak hands may not be able to actuate handle 102 if the maximum gripping force required to actuate handle 102 is greater than 35 N. However, handle 102 having a stroke length too short will result in difficultly performing delicate operations with tool 100 and using instrument assembly 171 in confined spaces. Therefore, handle 102 having a maximum gripping force less than 35 N and a stroke length less than 14 mm allows the user to maintain a grip on handle 102 to operate tool 100, resulting in less fatigue compared to other prior art tools, such as Conventional Technology 1 and Conventional Technology 2. The force measured in the graph of FIG. 9 occur when no tissue or objects are being grasped by instrument assembly 171.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal", "distal", "upper" and "lower" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

What is claimed is:

1. A surgical tool, comprising:
   a housing having a proximal end and a distal end, the housing including a guide rail;
   a yoke slidably coupled to the housing;
   a handle pivotally coupled to the housing, wherein pivoting of the handle towards the proximal end of the housing moves the yoke distally;
   a link coupling the handle to the housing, the link having a first end and a second end, the first end of the link rotatably coupled to the handle and the second end of the link rotatably coupled to the yoke and slidable within the guide rail;
   a yoke pivot pin pivotably coupling the second end of the link to the yoke; and
   a handle pivot pin coupling the link to the handle, wherein the handle pivot pin is disposed proximal compared to the yoke pivot pin.

2. The surgical tool of claim 1, wherein the guide rail is curved.

3. The surgical tool of claim 2, wherein the guide rail has a proximal end and a distal end, the proximal end of the guide rail being disposed below the distal end of the guide rail.

4. The surgical tool of claim 1, wherein the yoke pivot pin is distal to the handle pivot pin.

5. The surgical tool of claim 1, wherein the handle pivot pin is disposed proximate the proximal end of the housing compared to the yoke pivot pin.

6. The surgical tool of claim 1, wherein the handle includes a top and a bottom and the handle pivot pin is disposed closer to the bottom of the handle than the yoke pivot pin.

7. The surgical tool of claim 1, wherein the handle is coupled to the housing at a pivot point and the handle includes a top and a bottom, the handle pivot pin being disposed closer to the bottom of the handle than the pivot point.

8. The surgical tool of claim 1, wherein the handle is coupled to the housing at a pivot point and the handle includes a top and a bottom, the yoke pivot pin being disposed closer to the bottom of the handle than the pivot point.

9. The surgical tool of claim 1, wherein the guide rail includes a channel and the yoke pivot pin is disposed through the guide rail such that the yoke pivot pin slides within the channel.

10. The surgical tool of claim 1, wherein the yoke pivot pin includes a first end and a second end each being tapered.

11. The surgical tool of claim 1, wherein the yoke pivot pin extends through the yoke, the link, and the guide rail.

12. The surgical tool of claim 1 further comprising:
    a guide aperture that extends through the yoke, the guide aperture configured to receive the yoke pivot pin such that the yoke pivot pin is movable within the guide aperture during actuation of the handle.

13. The surgical tool of claim 1, wherein the yoke pivot pin includes a ring configured to contact the guide rail.

14. The surgical tool of claim 1, wherein guide rail includes a low-friction coating formed on a region of the guide rail where the yoke pivot pin contacts the guide rail.

15. The surgical tool of claim 1, wherein the handle has an initial position and an actuated position, the actuated position being when the handle is disposed proximate the proximal end of the housing compared to when the handle is in the initial position.

16. The surgical tool of claim 1 further comprising:
a grasper assembly disposed at a distal end of a shaft, the shaft extending form the distal end of the housing, wherein movement of the handle results in movement of the yoke causing actuation of the grasper assembly.

17. The surgical tool of claim 1 further comprising:
a guide assembly including a motor coupled to the yoke and configured to move the yoke.

18. The surgical tool of claim 1 further comprising:
an elongated shaft extending from the distal end of the housing; and
a grasping instrument disposed on a distal end of the elongated shaft, the grasping instrument coupled to the yoke such that movement of the yoke causes actuation of the grasping instrument.

19. A surgical tool, comprising:
a housing having a proximal end and a distal end, the housing including a guide rail;
a yoke slidably coupled to the housing between the proximal end and the distal end;
a handle pivotally coupled to the housing, wherein pivoting of the handle causes the yoke to move proximally and distally;
a link coupling the handle to the housing, the link having a first end and a second end, the first end of the link rotatably coupled to the handle and the second end of the link rotatably coupled to the housing by a yoke pivot pin, the yoke pivot pin being slidable within the guide rail and coupled to the yoke; and
a handle pivot pin coupling the link to the handle, wherein the handle pivot pin is disposed proximal to the yoke pivot pin,
wherein the guide rail is curved and includes a channel and the pivot pin is disposed through the guide rail such that the pivot pin slides within the channel.

20. A surgical tool, comprising:
a housing having a proximal end and a distal end, the housing including a guide rail, wherein the guide rail is curved;
a yoke slidably coupled to the housing;
a handle pivotally coupled to the housing;
a link coupling the handle to the housing, the link having a first end and a second end, the first end of the link rotatably coupled to the handle and the second end of the link rotatably coupled to the yoke and slidable within the guide rail;
a yoke pivot pin pivotably coupling the second end of the link to the yoke; and
a handle pivot pin coupling the link to the handle, wherein the handle pivot pin is disposed proximal compared to the yoke pivot pin;
wherein the guide rail is curved.

21. The surgical tool of claim 20, wherein the guide rail has a proximal end and a distal end, the proximal end of the guide rail being disposed below the distal end of the guide rail.

* * * * *